(12) United States Patent
Borgen et al.

(10) Patent No.: US 9,581,568 B2
(45) Date of Patent: Feb. 28, 2017

(54) SYSTEM FOR MEASURING PRESSURE AND TEMPERATURE

(75) Inventors: Harald Borgen, Horten (NO); David Christian Petersen, Åsgårdstrand (NO); Petter F. Schmedling, Moss (NO); Marius Bornstein, Oslo (NO); Trond Sjulstad, Svarstad (NO); Morten Roll Karlsen, Borrre (NO); Andreas Bjerknes Taranrød, Tønsberg (NO); Jan Martin Bendiksen, Drammen (NO); Tor Helge Brandsæter, Hvittingfoss (NO)

(73) Assignee: Techni AS, Borre (NO)

( * ) Notice: Subject to any disclaimer, the term of this patent is extended or adjusted under 35 U.S.C. 154(b) by 314 days.

(21) Appl. No.: 14/000,102

(22) PCT Filed: Feb. 16, 2012

(86) PCT No.: PCT/EP2012/052665
§ 371 (c)(1),
(2), (4) Date: Mar. 5, 2014

(87) PCT Pub. No.: WO2012/110588
PCT Pub. Date: Aug. 23, 2012

(65) Prior Publication Data
US 2014/0174187 A1 Jun. 26, 2014

(30) Foreign Application Priority Data
Feb. 16, 2011 (NO) .................................. 20110271

(51) Int. Cl.
*G01N 29/024* (2006.01)
*G01K 11/22* (2006.01)
(Continued)

(52) U.S. Cl.
CPC ........... *G01N 29/024* (2013.01); *G01K 11/22* (2013.01); *G01L 11/06* (2013.01);
(Continued)

(58) Field of Classification Search
USPC ................................ 73/708, 24.01, 702, 597
See application file for complete search history.

(56) References Cited

U.S. PATENT DOCUMENTS

| 5,289,436 | A | 2/1994 | Terhune |
| 5,542,298 | A | 8/1996 | Sarvazian et al. |

(Continued)

FOREIGN PATENT DOCUMENTS

| CA | 2 634 855 A1 | 12/2008 |
| CN | 201028977 Y | 2/2008 |

(Continued)

OTHER PUBLICATIONS

International Search Report for corresponding International Application No. PCT/EP2012/052665, mailed May 23, 2012 (3 pages).
(Continued)

*Primary Examiner* — Paul West
*Assistant Examiner* — Xin Zhong
(74) *Attorney, Agent, or Firm* — Osha Liang LLP (57) ABSTRACT

The present invention relates to system for measuring pressure and temperature based on change in the characteristic properties of a medium for ultrasound under the effect of pressure and temperature. The invention is based on two waveguides where geometry is adapted to the medium's characteristic properties for ultrasound such that only planar pressure waves are generated in the waveguides. The first of the waveguides is arranged for measuring temperature due to thermal expansion of the medium, where the medium is pressure-compensated by means of an internal compensator to prevent thermal pressure accumulation, and where mea-
(Continued)

suring temperature is based on the medium's specific known characteristic data for ultrasound under the effect of temperature under constant pressure. The second waveguide is arranged for measuring pressure, based on waveguide and the medium's known characteristic properties for thermal expansion and pressure, and where the thermal effect is corrected analytically based on measurement of temperature in the first channel. The physical principle of the invention is based on the properties of a medium (oil) where the stability for high temperature and pressure is crucial for long-term properties. Long-term properties of ultrasound sensors are not physically linked to the medium's properties, such that change in characteristic properties of ultrasound sensors does not impair the accuracy of the medium unless the function of the ultrasound sensors ceases. The physical principle of the invention allows an arrangement where ultrasound sensors can be separated from measuring channels by a pressure barrier, such that the integrity of the pressure barrier is not broken.

17 Claims, 4 Drawing Sheets

(51) Int. Cl.
  *G01L 11/06* (2006.01)
  *G01L 19/00* (2006.01)
  *G01N 29/036* (2006.01)
  *G01N 29/32* (2006.01)
(52) U.S. Cl.
  CPC ........ *G01L 19/0092* (2013.01); *G01N 29/036* (2013.01); *G01N 29/323* (2013.01); *G01N 29/326* (2013.01); *G01N 2291/02872* (2013.01); *G01N 2291/02881* (2013.01)

(56) References Cited

U.S. PATENT DOCUMENTS

| | | | |
|---|---|---|---|
| 6,394,647 | B1 | 5/2002 | Allmendinger et al. |
| 7,266,989 | B2* | 9/2007 | Ariav ................... G01N 29/024 374/119 |
| 2002/0143480 | A1 | 10/2002 | Komatsu et al. |
| 2004/0020299 | A1* | 2/2004 | Freakes ................. G01L 9/0025 73/702 |
| 2005/0252294 | A1 | 11/2005 | Ariav |
| 2008/0310478 | A1* | 12/2008 | Mulders ................. G01K 11/24 374/142 |
| 2009/0245323 | A1 | 10/2009 | Brummel et al. |

FOREIGN PATENT DOCUMENTS

| | | |
|---|---|---|
| WO | 9832378 A1 | 7/1998 |
| WO | 99/05494 A1 | 2/1999 |

OTHER PUBLICATIONS

Written Opinion for corresponding International Application No. PCT/EP2012/052665, mailed May 23, 2012 (3 pages).
International Preliminary Report on Patentability for corresponding International Application No. PCT/EP2012/052665, mailed May 21, 2013 (12 pages).
Reeder et al.: "Surface-Acoustic-Wave Pressure and Temperature Sensors", Proceedings of the IEEE, vol. 64, No. 5, May 1976, pp. 754-756 (3 pages).
Norwegian Search Report for No. 20110271 dated Sep. 16, 2011 (1 page).
Espacenet Publication Abstract for CN201028977, publication date Feb. 27, 2008 (1 page).
Espacenet Publication Abstract for WO9905494, publication date Feb. 4, 1999 (2 pages).

* cited by examiner

SYSTEM FOR MEASURING PRESSURE AND TEMPERATURE

The present invention relates to a system for measuring pressure and temperature in an oil well based on direct or indirect transit time measurements by ultrasound. More specifically, the present invention relates to a system that can be arranged as a resonance element with an electric resonance that is proportional to the change in density and sound velocity in a medium due to the effect of pressure and temperature.

The system for measuring pressure and temperature according to the present invention comprises two measuring channels in the form of tubes, which are filled with a medium in liquid state, where geometry is provided for planar pressure waves. A first measuring channel (a) measures change in sound velocity through a medium due to temperature, and a second measuring channel (b) measures change in sound velocity through a medium due to pressure and temperature. The pressure is calculated by analytically subtracting a measured signal for temperature from a measured signal for pressure and temperature.

The background of the invention is the need for a sensor capable of measuring pressure and temperature in a well with high pressure and temperature. In connection with, for example, the production of hydrocarbons, it is desirable in oil and/or gas wells to use sensors and/or instruments that can be located on the outside or the inside of the accessible annulus in the well, to allow characteristic data such as pressure and temperature to be measured. At the same time, it is desirable that the sensor should not need external supply of energy by means of power cables or the like, which requires barrier-breaking devices, or batteries which have a time-limited useful life. An absolute requirement for equipment installed in oil and/or gas wells is that of robustness for ambient temperature, pressure and desired lifetime. If a technique involving complex electronics is used, it is usually not possible to satisfy the requirement of temperature, accuracy over time and lifetime fully. These properties are closely related to the type of electronics used. The invention's properties over time are stable because stability of the medium in waveguides is not affected by the properties of ultrasound sensors and that the physical properties of the measuring medium are almost constant over time.

A number of patents exist for measuring pressure and temperature in surroundings with high pressure and temperature that are intended for use in oil and/or gas wells. A common feature of most of these measuring systems is that they use a device with a piezocrystal or resonator, which undergoes a change in resonant frequency due to the effect of pressure and temperature. In contrast to these applications, the system according to the present invention uses known properties of a medium in liquid state in order to measure pressure or temperature indirectly.

Moreover, a number of applications exist that are based on use of ultrasound in a waveguide in order to measure physiological properties or fractions of mixtures. Typical utilisations may be:

Sound velocity
Concentration/incorporation of medium due to absorption of ultrasound where frequency together with returned intensity is used.
Precipitation of chemical compounds
Non-linear waves and change in wave shape
Measurement of speed (time) of chemical reactions U.S. Pat. No. 5,289,436 from 1994 is a known patent in which a medium in liquid state is used for transmission of ultrasound in a waveguide. In this patent a thin-walled tube of metal or plastic is used as an extension of an ultrasonic transducer for determining defects in material in geometrically inaccessible locations. This patent is merely a device for guiding ultrasound to the desired location with as little attenuation as possible due to viscosity in the medium (water), where minimum transmission of sound to waveguide is obtained by using a thin-walled tube, typically of a thickness of 0.1-0.3 mm. This patent is used to measure properties in the form of material faults in or on an object that is located outside the actual waveguide. Unlike U.S. Pat. No. 5,289,436, the present invention utilises the change in known characteristic properties of a medium under the effect of temperature and/or pressure, in order to measure pressure and temperature. A similar general utilisation of several parallel waveguides for ultrasound is described in Canadian Patent Application CA 2,634,855 (A1), where a mat with waveguides transverse to the main surface of the mat is used to obtain unidirectional parallel compression waves against an object that is to be examined, for example, a human body.

A further example of known patents in which a medium in liquid or gas state is used for ultrasound measurement is U.S. Pat. No. 7,266,989 B2 from 2007. In this patent, several separate chambers are used for measuring physical and chemical properties of a surrounding medium. In this patent, an ultrasonic transmitter and an ultrasonic receiver are used for each measuring chamber, where transit time measurements are used. The primary task of the patented system is to measure chemical composition and temperature. The device for measuring pressure is made having a flexible membrane, where pressure is measured on the basis of change of distance between ultrasonic transmitter and ultrasonic receiver in an elastomeric strip (plastic), which is fastened to the surface of the flexible membrane on an opposite side to a surrounding medium which exerts pressure on the membrane. There is gas in one space behind the membrane (opposite the pressure side), such that the elastomeric strip with ultrasonic transmitter and ultrasonic receiver can move freely.

This way of carrying out pressure measurement is classical in relation to pressure transducers based on piezocrystals where the piezo element is replaced by an ultrasonic transmitter and an ultrasonic receiver.

The aforementioned solution will however be complex and will not always give correct measurements, in view of the fact that properties of the system will not be constant over time.

The object of the invention is to remedy or reduce at least one of the disadvantages of the prior art.

A further object of the present invention will be to provide a simpler and more reliable system.

These objects are obtained by means of a system for measuring pressure and temperature, which is based on direct or indirect transit time measurements, as disclosed in the following independent claim 1, with additional features of the invention set forth in the dependent claims and the description below.

In contrast to the patents referred to, the present invention is based on measuring pressure and temperature on the basis of direct and indirect transit time measurements in two or more waveguides, where the measurement is done using ultrasound in the form of planar pressure waves in a known medium (for example, oil), contained within its respective waveguide. In the invention, an ultrasonic transmitter and an ultrasonic receiver are integrated in the same unit and referred to as an ultrasonic transducer. The present invention is based on two waveguides where a waveguide (a) is arranged for measuring temperature due to thermal expansion of the medium, which directly alters the medium's characteristic properties such as density, sound velocity and ultrasonic impedance, and where the medium is pressure-compensated by an internal compensator (for example, a bellows or the like) filled with gas or other readily compressible material, and a waveguide (b) which is arranged for measuring pressure, based on that the thermal expansion of the medium and the effect of pressure directly or indirectly on the medium in the measuring channel alters characteristic properties such as density, sound velocity and ultrasonic impedance, and in that the effect due to temperature measured using waveguide (a) is corrected analytically based on known properties of the sensor's medium (oil). Unlike the known patents where the measuring channels and ultrasonic transmitter/receiver are arranged in the same unit, the inventive sensor for ultrasound can be separated from the actual measuring channels such that the integrity of a medium's surroundings in the form of a pressure barrier is not broken (penetrated) in any way. The physical principles of the invention are based on the properties of a medium (oil), where stability to high temperature and pressure is crucial for long-term properties. These physical principles for the medium (oil) are not linked to ultrasound as a measuring method, such that long-term stability is inherent in relation to the medium and not the ultrasonic transducer.

The present invention may also be applied as an independent unit for measuring pressure and temperature where the desire for a long-term stable system for high pressure and temperatures is requisite. At the same time, the present invention has the property that energy in the measured signal (the electric response) is only based on the supplied energy that is applied to each of the measuring channels without the supply of additional energy. The system can be arranged with common electric conductors from an instrument to ultrasonic transducers, such that a common time-variable electric signal (voltage) is applied to each measuring channel simultaneously. This arrangement requires the length of the measuring channels (waveguides) to be different, such that the return signal is separated in time. The system may also be arranged with a common ultrasound sensor for the two measuring channels, where ultrasound can be split into two separate channels, or that one channel is arranged on either side of the ultrasonic transducer, such that ultrasound is emitted simultaneously in two measuring channels lying on the same level with a common ultrasonic transducer.

A type of property that is desired in a sensor for measuring physical states is the capacity of making measurements based on a time-variable signal and sending back a time-variable signal.

The term "pressure compensator" according to the present invention should be understood to mean a flexible device which contracts or expands in such a way that a constant pressure is maintained in the pressure compensator or an element in which the pressure compensator is arranged. The pressure compensator may typically contain a spiral spring, gas or the like in a flexible housing. Furthermore, a device that converts ambient pressure could be a flexible barrier that transfers pressure directly to a medium, or a mechanical device in the form of a spring that is altered a certain distance, such that the resonance or transit time for a measuring channel is changed.

The invention will now be explained in connection with several embodiments with reference to the attached figures, wherein.

Figure 1:
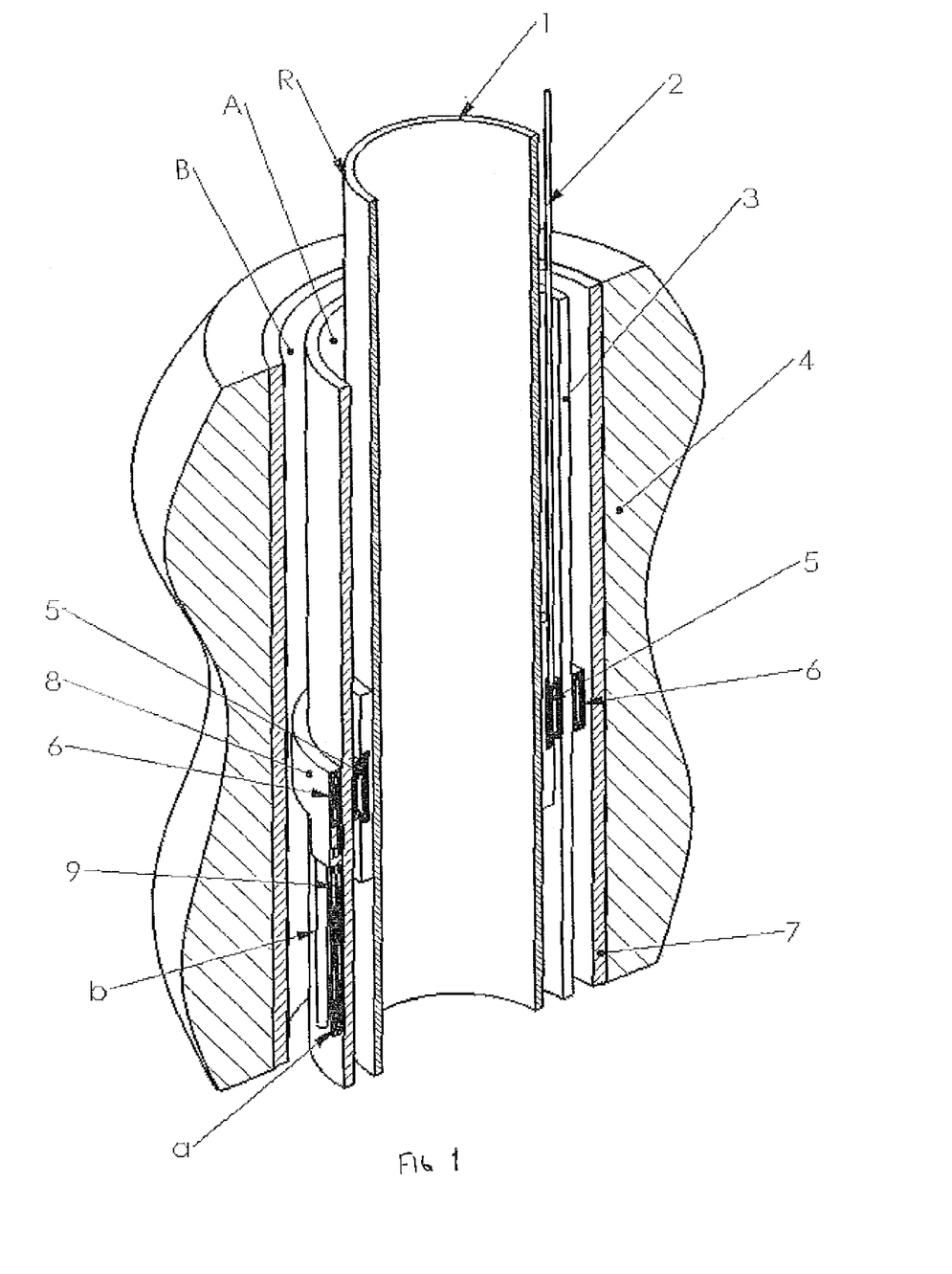
FIG. 1 shows a first embodiment of the present invention.

In a typical application of the system for measuring pressure and temperature based on the use of ultrasound according to the present invention, the system can be used for measuring pressure and temperature in the annulus of an oil and/or gas well without using barrier-breaking devices, as shown in FIG. 1.

A sensor 8 based on the use of ultrasound is arranged in an annulus B in the oil and/or gas well. The sensor 8 measures pressure and temperature based on a change in sound velocity due to the effect of the pressure and temperature which are in a fluid in the annulus B. The sensor 8 comprises two measuring channels (a) and (b) which are appropriately configured as regards tube diameters, signal converters for ultrasound (ultrasonic emitter) and medium (oil). The first measuring channel (a) has compensation for pressure variations, where this is based on an enclosed volume that is delimited by a bellows 3 which is filled with a flexible medium (gas) and which responds with a constant pressure in response to thermal volume variations, and will only register change of sound velocity due to temperature changes as a result of ambient temperature. The second measuring channel (b) will be affected by pressure through the bellows 3 and temperature equal to ambient. Measurement of temperature is made directly using transit time measurements in the first measuring channel (a). Measurement of pressure in the second measuring channel (b) is made using transit time measurements, and in that the effect due to temperature that is measured in measuring channel (a) is subtracted from the measurement result obtained in measuring channel (b), the above-mentioned measurement will only be affected by pressure. The system according to the present invention is shown here interconnected with a induction and resonance device 5, 6, which is so configured that the induction and resonance device 5, 6 is able transmit a time-variable signal with sufficient energy for the measurement through a pipe wall R, and which is further connected to an instrument (not shown) via an electric cable 2. During measurement, an electric time-variable signal will be generated in the instrument, where this electric time-variable signal will be transmitted to the ultrasound sensors 8 via the electric cable 2 and the induction and resonance device 5, 6. The ultrasound sensors 8 may comprise an ultrasound oscillator element (not shown). When the time-variable electric signal excites the two ultrasonic transducers 8 in the first and second measuring channels (a), (b), pressure waves will be generated in the measuring channel medium 9 (oil), which propagate along the measuring channels at the characteristic sound velocity in the medium 9 for each of the measuring channels. The pressure waves (ultrasound) will be reflected back from the end of the measuring channels, such that the returned ultrasound again excites the ultrasonic emitters 8 to generate a voltage that is staggered timewise in relation to transit time for the ultrasound. This generated voltage is sent back to the instrument via the induction and resonance device 5, 6 and the cable 2. The system for measuring pressure and temperature according to the present invention will thus have the property that the energy in the driving signal (the generated electric time-variable signal) is returned by way of response from measuring channels without the supply of additional energy.

Figure 2:
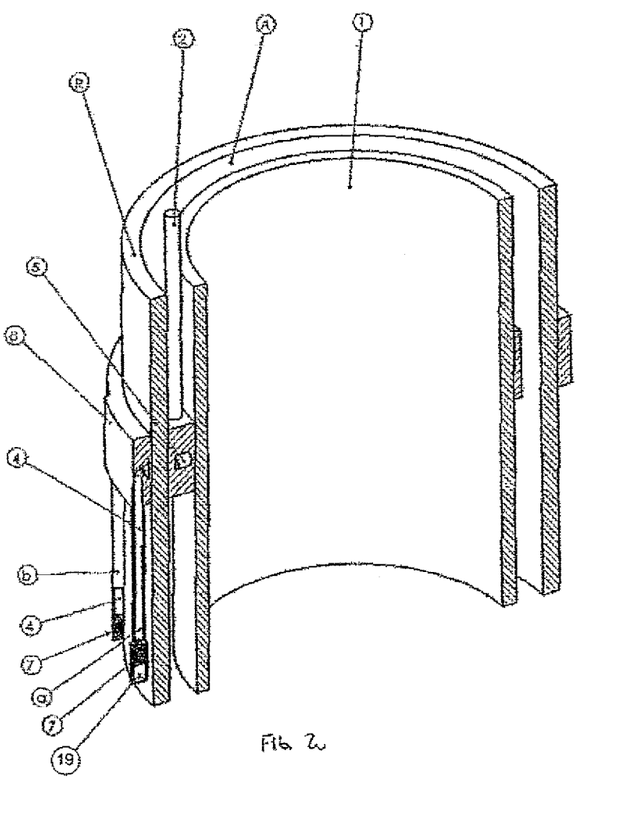
FIG. 2 shows a second embodiment of the present invention.

In another embodiment, the system for measuring pressure and temperature according to the present invention can be applied in the following way with reference to FIG. 2. A sensor 8 with two measuring channels (a) and (b) based on ultrasound is located in annulus B surroundings where it is desired to measure pressure and temperature. This sensor 8 measures pressure and temperature based on change in characteristic properties of ultrasound under the effect of pressure and temperature. The sensor 8, like that described in connection with FIG. 1, comprises a first and a second measuring channel (a), (b), which first and second measuring channels (a), (b) are identical as regards tube diameter and medium 9 (oil). The length of the measuring channels (a), (b) is adjusted freely according to a number of different factors.

One of the measuring channels (a) has compensation for pressure variations by means of bellows 7 and an enclosed medium 19 (gas) which ensures a constant pressure internally as a result of thermally conditioned volume variation in the medium, and will only register change in characteristic properties due to temperature changes equal to ambient.

The other associated measuring channel (b) will be affected by both pressure and temperature equal to ambient. Measurement of temperature is based on change in characteristic properties for ultrasound owing to temperature variation in measuring channel (a). Measurement of pressure in measuring channel (b) is based on change in characteristic properties for ultrasound due to temperature and pressure variation where the effect of temperature is compensated analytically with the aid of measurement results in (a), such that only the effect of pressure remains. In this embodiment of the invention, ultrasound sensors 5 are located in an annulus A, such that the need for an induction and resonance device 5, 6 or a penetrator (not shown) through a pipe R is not necessary. Ultrasound sensor 5 will then, via an electric cable 2, be connected to an instrument (not shown) that is located outside the annulus A. During measurement, an electric time-variable signal that is generated in the instrument is transmitted to ultrasound sensors 5 via the electric cable 2. In this embodiment of the invention, ultrasound sensors are to be considered as an integral part of pipe R. When the time-variable electric signal excites ultrasound sensor 5, pressure waves (ultrasound) will be generated which are transmitted to medium 9 (oil) in measuring channels (a), (b), where the pipe is a part of the ultrasound matching material in ultrasound sensor 1. The pressure waves will propagate along the measuring channels (a), (b), with characteristic sound velocities for each of the channels. The pressure waves (ultrasound) will be reflected back from the end of the measuring channels (a), (b), such that the pressure waves again propagate back to oscillator elements (not shown) in the ultrasound sensors in ultrasound sensor 5. When the oscillator element is subjected to the returned ultrasound, a voltage will be generated that is staggered timewise in relation to the transit time for the ultrasound. This generated voltage is sent back to the instrument (not shown) via the electric cable 2. The aforementioned solution may also be used in connection with distance measurements to an ultrasound mirror, movable in relation to the direction of the distance at one end of the channel where the distance represents the compression in a bellows or membrane 3 subjected to ambient pressure and/or temperature, as shown in FIG. 4.

Figure 3:
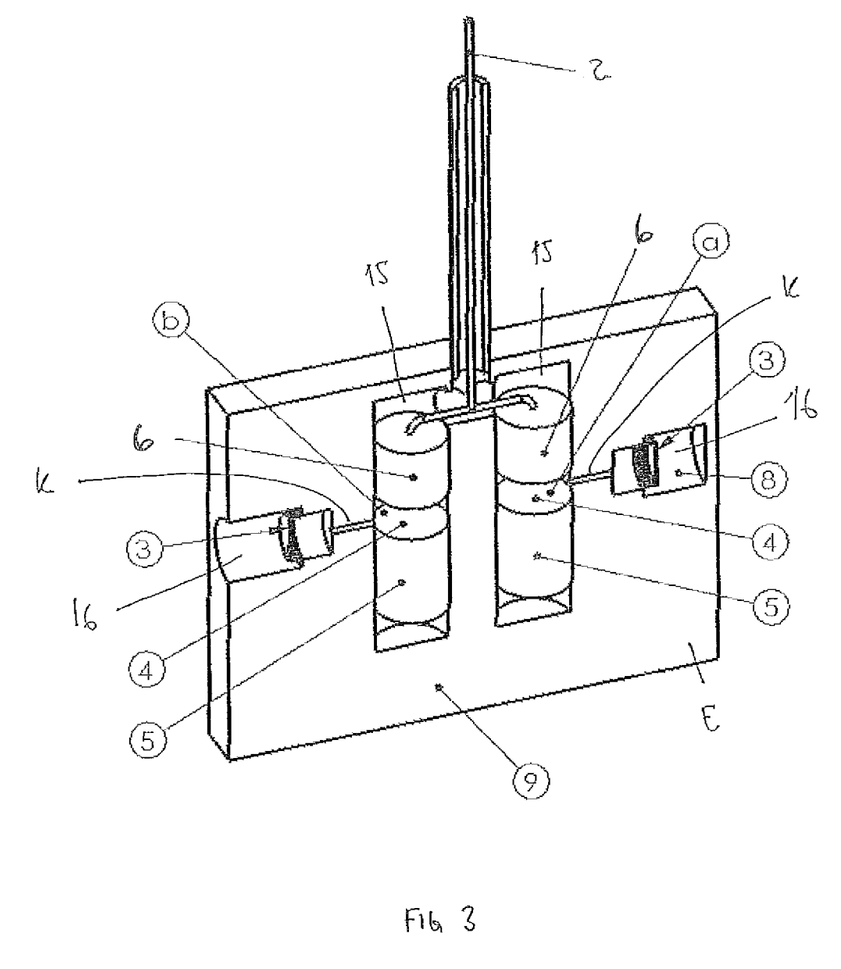
FIGS. 3 and 4 show details of the present invention.
Figure 4:
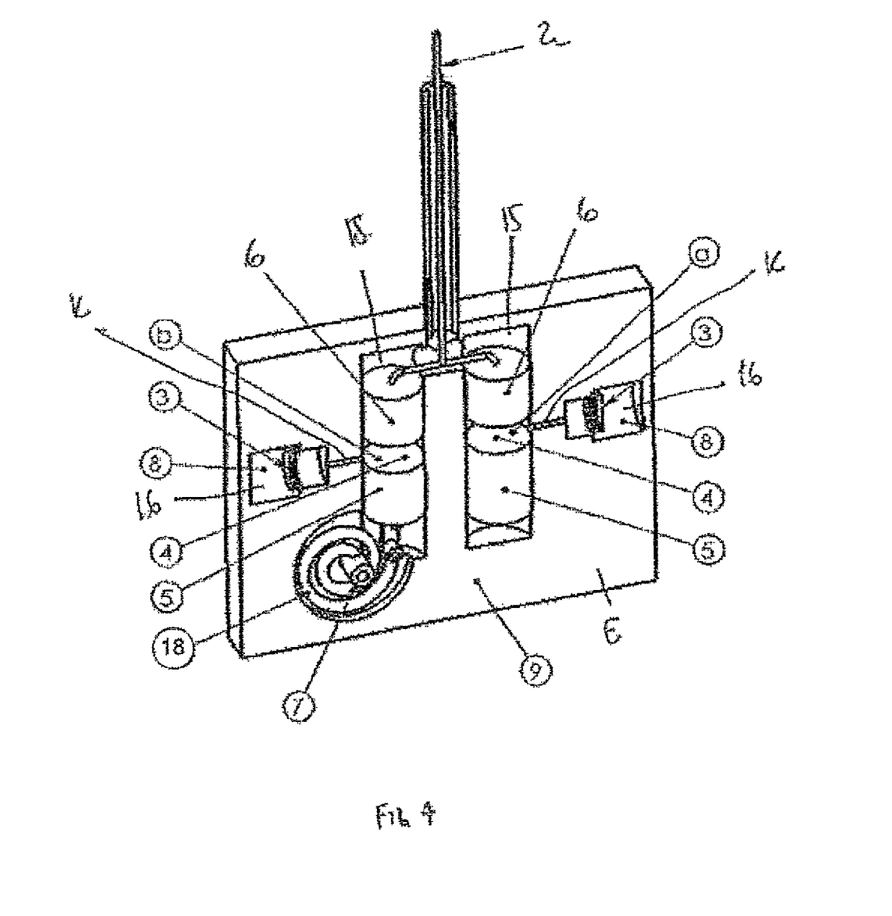

FIGS. 3 and 4 show how the system for measuring pressure and temperature according to the present invention can be arranged, where it is shown that induction and resonance devices 5, 6 consisting of an ultrasonic transducer 6 and an ultrasonic transmitter 5, are arranged in recesses 15 in an element E. Each ultrasonic transducer 6 is further connected to the electric cable 2. The ultrasonic transducers 6 and the ultrasonic emitters 5 are further so arranged in the recesses 15 that a space or a gap 4 is formed between them. Two other recesses 16 are also formed in the element E, the two recesses 15, 16 being connected to each other through a channel K. The channels K are further so arranged that they open into the space or gap 4. In FIG. 3, one of the recesses 16 will be open to the surrounding medium, whilst the other recess 16 will be "closed". In FIG. 4 both recesses 16 are closed. In each of the recesses 16 there is further arranged a bellows 3.

In FIG. 4, the embodiment will also comprise a bourbon tube 18 which under the effect of a pressure applied via an inlet 7 will be actuated such that the bourbon tube 18 is uncoiled or coiled.

In another embodiment, the system for measuring pressure and temperature according to the present invention can be applied in the following way: A sensor 9 with two measuring channels (a) and (b) based on ultrasound is located at a desired point that is subjected to pressure and temperature. This sensor 9 measures pressure and temperature based on change in sound velocity under the effect of pressure and temperature. The system consists of two measuring channels (a) and (b) in the form of gaps 4 in a tube filled with medium in liquid state where geometry is arranged for planar pressure waves in the medium (oil). One of the measuring channels (a) has compensation for pressure variations internally by means of bellows 3 and an enclosed volume (gas) 8, and will only register change of sound velocity due to temperature changes equal to ambient. The other associated measuring channel (b) will be affected by both pressure and temperature equal to ambient. The basic principle for measuring pressure and temperature is to use a medium (oil) as impedance matching means between ultrasound sensor 2 and an attenuating material 5 which is shown here in the form of a cylinder. The impedance of a medium is defined as density multiplied by sound velocity (formula $Z=\rho \cdot v$). According to the theory for ultrasound, the ultrasound transfer as regards transmission and reflection can be optimised in order to eliminate reflection. This is done by introducing an intermediate layer that matches ultrasound impedance between the two materials through a third material (oil). The requirement for this intermediate layer is that the ultrasound impedance is equal to the square root of the product of the ultrasound impedance for respective materials on each side that is to be matched, that is to say, that reflection or transmission of ultrasound is dependent on the frequency of the pressure waves, the distance in the gap (thickness of gaps 4) and the ultrasound properties of the intermediate layer and the materials in the induction and resonance device 5, 6. The requirement to allow maximum transmission to be obtained is given by the formula $Z_{oil(4)} = \sqrt{Z_{ultra(3)} \cdot Z_{atten(5)}}$. The thickness of the intermediate layer or the gaps 4 must be equal to ¼ wave length for optimal transmission. The actual measurement of pressure and temperature can be done in two ways, where method 1 is an embodiment in which material in the ultrasound sensor 5 acts as an attenuating material such that transmitted ultrasound (in the gap) ceases at a specific frequency and its harmonic frequencies.

Method 2 is that material in the ultrasound sensor 5 functions as a mirror/reflector for ultrasound, and where the returned ultrasound intensity is maximised by a specific frequency and its harmonic frequencies.

The properties of measuring channel 4 are known and temperature and pressure can subsequently be calculated when the form of the measured response/frequency curve from the sensor is known, Typically, intensity responses from a series of measurements are interpolated in order to find the exact resonance frequency. When ultrasound sensors are subjected to the returned ultrasound, a voltage will be generated that is proportional to reflected ultrasound. This generated voltage is sent back to the instrument via the electric cable 2. If measuring channels (a) and (b) are to use common electric conductors in cable 2, the range for response frequencies in each of the measuring channels must be constructed so that they are not overlapped in frequency range.

In another embodiment, the invention can be applied in the following way: a sensor 9 with two measuring channels (a) and (b) is placed at a desired location where measurement of pressure and temperature is required. This sensor measures pressure and temperature based on change in characteristic properties for ultrasound impedance in a medium-filled gap 4, as in the case shown in FIG. 3. Measuring channel (a) is based on change in characteristic properties for temperature and has compensation for pressure variations due to thermal volume expansion in the medium (oil), here shown as a bellows 3 and a compressible medium 8 (gas) which ensures an almost constant pressure due to the thermal expansion of the medium (oil) in the measuring channel gap 4.

Measuring channel (b) has compensation for pressure variations in a medium (oil) due to temperature as described for measuring channel (a), but has in addition a bourbon tube 18 (manometer) which, when subjected to an internal pressure via inlet 7, will uncoil such that the cylinder 5 becomes axially offset with a mechanism (not shown) such that distance in the gap 4 increases.

The basic principle for measuring pressure and temperature is to use a medium (oil) as an impedance matching between ultrasound transducer 6 and a reflecting or attenuating material 5, as explained under FIG. 3. The actual measurement of pressure and temperature can be done in two ways, where method 1 is that the material in the ultrasound sensor 5 acts as an attenuating material such that transmitted ultrasound ceases at a specific frequency and its harmonic frequencies. Method 2 is that material in the ultrasound sensor 5 functions as a mirror/reflector for ultrasound and returned ultrasound intensity is maximised at a specific frequency and its harmonic frequencies, as described for FIG. 3.

The impedance of a medium is defined as density multiplied by sound velocity (formula: $Z=\rho \cdot v$). According to ultrasound theory, the ultrasound transfer as regards transmission and reflection can be optimised in order to eliminate reflection. This is done by introducing an intermediate layer in a gap 4 that is matched to the impedance between the two materials. The requirement for this intermediate layer is that the impedance is equal to the square root of the product of impedance for respective materials on each side that is to be matched. This means to say that reflection or transmission of ultrasound is dependent on the frequency of the pressure waves, the distance in the gap (thickness of gaps 4) and the ultrasound properties of the intermediate layer and materials in the induction and resonance device 5, 6. The requirement for achieving maximum transmission is given by the formula $Z_{oil(4)} = \sqrt{Z_{ultra(3)} \cdot Z_{atten(5)}}$. The thickness of the gap 4 must be equal to ¼ wave length for optimal transmission. The actual measurement of pressure and temperature is done by adjusting the frequency of ultrasound so that reflected ultrasound ceases or is minimal. The properties of the medium in gap 4 are known and temperature and pressure may subsequently be calculated when the resonance frequencies in each of the measuring channels are known. Typically, the frequency/resonance curve from a series of measurements will be interpolated in order to calculate the most exact frequency possible. When the ultrasonic transmitters are subjected to the reflected ultrasound, a voltage will be generated that is proportional to the portion of reflected ultrasound. This generated voltage is sent back to the instrument via cable 2. If measuring channels (a) and (b) are to use common electric conductors in the cable 2, the range for response frequencies in each of the measuring channels must be constructed such that they are not overlapped in frequency range. Typically, this embodiment of the invention for pressure measurement will mean that the breadth of the frequency range can more easily be adjusted to the desired range. The aforementioned solution can also be used for distance measurements for a mirror movable in the direction of the distance at one end of the channel where the distance represents the compression in a bellows or membrane subjected to ambient pressure or temperature where the measuring principle for pressure measurement is transit time.

The invention has now been explained with reference to several embodiments. A person of skill in the art will understand that a number of changes and modifications may be made to the illustrated embodiments which fall within the scope of the invention as defined by the following claims.

The invention claimed is:

1. A system for measuring pressure and temperature based on ultrasound, the system comprising:
    a sensor comprising two separate measuring channels being in the form of a space or gap, and an ultrasonic transducer, the ultrasonic transducer being arranged in recesses to transmit and receive ultrasound to and from the two separate measuring channels,
    said measuring channels containing a medium in liquid state whose pressure and temperature properties are known,
    wherein a first measuring channel of the two separate measuring channels is separated from a surrounding pressure of the measuring channels and wherein the first measuring channel is filled with a flexible medium and has an internal pressure compensator by a bellows for eliminating pressure accumulation due to temperature expansion, and wherein temperature is measured due to change in the properties of the medium for ultrasound, said change being measured by transit time or resonance frequency,
    a second measuring channel of the two separate measuring channels comprising a flexible bellows being open to a surrounding medium and wherein the flexible bellows in the second measuring channel transfers ambient pressure into a change in the properties of the second measuring channel for transit time or resonance frequency in the medium, and
    wherein temperature measurement in the first measuring channel is used to correct temperature effect on pressure measurement in the second measuring channel.

2. The system according to claim 1, wherein measuring channels for pressure and temperature are physically separated from ultrasound oscillator elements by a barrier, said barrier acting as an integral part of the ultrasound sensor.

3. The system according to claim 1, wherein measuring channels for pressure and temperature are physically separated from the ultrasonic transducer but is connected to the measuring channels in the form of solid rods, wherein the ultrasonic transducer communicates with measuring channels through said solid rods.

4. The system according to claim 1, wherein the first measuring channel for temperature is based on temperature expansion under constant pressure where change in density results in a change in sound velocity that is measured by change in transit time.

5. The system according to claim 1, wherein the first measuring channel for temperature is based on temperature expansion under constant pressure where change in density results in a change in sound velocity, wherein both density and sound velocity alter the impedance of the medium, which in turn excites a measurable resonance frequency between two media, the resonance frequency being a known constructed state due to temperature in the medium.

6. The system according to claim 1, wherein the second measuring channel for pressure is based on change in density due to compression, which in turn leads to a change in sound velocity, said change being measured by transit time measurement for ultrasound where the temperature effect of the medium is corrected by temperature measured in the first measuring channel for temperature.

7. The system according to claim 1, wherein the second measuring channel for pressure is based on change in density due to compression which in turn leads to a change in sound velocity, wherein change in the ultrasound impedance of the medium due to variation in density and sound velocity that is measured by the change in response is based on characteristic-constructed resonance frequency, wherein correction is made for temperature effect measured in the first measuring channel for temperature.

8. The system according to claim 1,
wherein a measuring channel for pressure is based on a pressure-proportional mechanical change in length of a waveguide, and where constant pressure in a medium of the waveguide is provided by constant pressure compensation, and
wherein the first measuring channel provides temperature compensations due to temperature impact for the change in length, the change in length being measured by transit time.

9. The system according to claim 2,
wherein a measuring channel for pressure is based on a pressure-proportional mechanical change in length of a waveguide, and where constant pressure in a medium of the waveguide is provided by constant pressure compensation, and
wherein the first measuring channel provides temperature compensations due to temperature impact for the change in length, the change in length being measured by transit time.

10. The system according to claim 3,
wherein a measuring channel for pressure is based on a pressure-proportional mechanical change in length of a waveguide, and where constant pressure in a medium of the waveguide is provided by constant pressure compensation, and
wherein the first measuring channel provides temperature compensations due to temperature impact for the change in length, the change in length being measured by transit time.

11. The system according to claim 4,
wherein a measuring channel for pressure is based on a pressure-proportional mechanical change in length of a waveguide, and where constant pressure in a medium of the waveguide is provided by constant pressure compensation, and
wherein the first measuring channel provides temperature compensations due to temperature impact for the change in length, the change in length being measured by transit time.

12. The system according to claim 5,
wherein a measuring channel for pressure is based on a pressure-proportional mechanical change in length of a waveguide, and where constant pressure in a medium of the waveguide is provided by constant pressure compensation, and
wherein the first measuring channel provides temperature compensations due to temperature impact for the change in length, the change in length being measured by transit time.

13. The system according to claim 1,
wherein a measuring channel for pressure is based on direct proportional mechanical change in length of a waveguide, where constant pressure in a medium of the waveguide is provided by pressure compensation, and where change in pressure-proportional length is measured by the change in constructed resonance frequency where correction is made for temperature effect measured in the measuring channel for temperature.

14. The system according to claim 2,
wherein a measuring channel for pressure is based on direct proportional mechanical change in length of a waveguide, where constant pressure in a medium of the waveguide is provided by pressure compensation, and where change in pressure-proportional length is measured by the change in constructed resonance frequency Where correction is made for temperature effect measured in the measuring channel for temperature.

15. The system according to claim 3,
wherein a measuring channel for pressure is based on direct proportional mechanical change in length of a waveguide, where constant pressure in a medium of the waveguide is provided by pressure compensation, and where change in pressure-proportional length is measured by the change in constructed resonance frequency where correction is made for temperature effect measured in the measuring channel for temperature.

16. The system according to claim 4,
wherein a measuring channel for pressure is based on direct proportional mechanical change in length of a waveguide, where constant pressure in a medium of the waveguide is provided by pressure compensation, and where change in pressure-proportional length is measured by the change in constructed resonance frequency where correction is made for temperature effect measured in the measuring channel for temperature.

17. The system according to claim 5,
wherein a measuring channel for pressure is based on direct proportional mechanical change in length of a waveguide, where constant pressure in a medium of the waveguide is provided by pressure compensation, and where change in pressure-proportional length is measured by the change in constructed resonance frequency where correction is made for temperature effect measured in the measuring channel for temperature.

* * * * *